United States Patent [19]

Burgess

[11] Patent Number: 5,410,086
[45] Date of Patent: Apr. 25, 1995

[54] SELECTIVE PREPARATION OF DIETHYLENETRIAMINE

[76] Inventor: Lloyd M. Burgess, 1107 Ivywood La., South Charleston, W. Va. 25309

[21] Appl. No.: 719,683

[22] Filed: Jun. 25, 1991

Related U.S. Application Data

[63] Continuation of Ser. No. 373,313, Jun. 27, 1989, abandoned.

[51] Int. Cl.$^6$ ............... C07C 209/16; C07C 209/64; C07C 209/00
[52] U.S. Cl. ................... 564/470; 544/358; 544/401; 544/402; 564/479; 564/480
[58] Field of Search ......... 564/470, 480, 479; 544/401, 402, 358

[56] References Cited

U.S. PATENT DOCUMENTS

| | | | |
|---|---|---|---|
| 2,781,389 | 2/1957 | Mannheimer | 260/458 |
| 2,861,995 | 11/1958 | MacKenzie | 260/268 |
| 3,068,290 | 12/1962 | Lichtenberger et al. | 260/535 |
| 3,112,318 | 11/1963 | Lemon et al. | 564/480 |
| 3,285,920 | 11/1966 | Muhlbaur et al. | 544/402 |
| 3,714,259 | 1/1973 | Lichtenwalter et al. | 260/583 P |
| 4,036,881 | 7/1977 | Brennan et al. | 260/583 P |
| 4,234,730 | 11/1980 | McConnell et al. | 544/358 |
| 4,547,591 | 10/1985 | Brennan et al. | 564/479 |
| 4,568,746 | 2/1986 | Cowherd, III | 544/358 |

FOREIGN PATENT DOCUMENTS 1508460 4/1978 United Kingdom.

*Primary Examiner*—Peter O'Sullivan

[57] ABSTRACT

This invention relates to a method for controlling the weight ratio of diethylenetriamine to piperazine in a process in which ethylenediamine, or a mixture of ethylenediamine and monoethanolamine, and hydrogen are maintained in the presence of a hydrogenation catalyst, which method comprises adjusting the hydrogen concentration in the liquid phase in an amount sufficient to effectuate control of the weight ratio of diethylenetriamine to piperazine in said process.

31 Claims, 2 Drawing Sheets

SELECTIVE PREPARATION OF DIETHYLENETRIAMINE

This application is a continuation of prior U.S. application Ser. No. 07/373,313 filed Jun. 27, 1989, now abandoned.

BRIEF SUMMARY OF THE INVENTION

1. Technical Field

This invention relates to a process for the production of an amine composition containing a high yield weight ratio of diethylenetriamine to piperazine and also to a method for controlling the weight ratio of diethylenetriamine to piperazine.

2. Background of the Invention

Low molecular weight, linear, polyalkylene polyamines are known for their many uses in industry. For example, U.S. Pat. No. 2,781,389 discloses the use of such linear polyalkylene polyamines to form detergent sulfonic acids and sulfate salts of amphoteric detergents.

U.S. Pat. No. 2,781,389 discloses that such linear polyalkylene polyamines can be produced by reacting ethylene oxide with ammonia. The patent fails to disclose any operable reaction conditions or useful catalysts for such a reaction. U.S. Pat. No. 3,068,290 discloses that monoethanolamine may be treated with ammonia at elevated temperatures in the presence of Raney nickel catalyst to produce an amine composition that is composed mainly of the monoalkylene polyamine, ethylenediamine, but which does contain some polyalkylene polyamines, e.g., diethylenetriamine and piperazine, in roughly equal minor amounts.

Because a linear polyalkylene polyamine such as diethylenetriamine and a cyclic polyalkylene polyamine such as piperazine do not have the same industrial uses and demands, it has been recognized that it would be desirable to develop a process with sufficient selectivity in forming a linear polyalkylene polyamine to produce an amine composition with a relatively high ratio of diethylenetriamine to piperazine. For example, U.S. Pat. No. 4,036,881 discloses that a phosphorous-containing compound will catalyze the reaction of ethylenediamine with monoethanolamine at temperatures between 250° C. and 350° C. to yield an amine composition that may have a high ratio of diethylenetriamine to piperazine. However, the high temperatures and pressures employed in U.S. Pat. No. 4,036,881 may be undesirable in given process stream.

Processes which produce amine compositions at temperatures lower than those in U.S. Pat. No. 4,036,881 are described in U.S. Pat. No. 3,714,259 and British Patent No. 1,508,460. U.S. Pat. No. 3,714,259 discloses that ethylenediamine will react with monoethanolamine in the presence of a nickel, copper, iron, palladium, platinum, cobalt, chromium, rhodium, molybdenum or titanium catalyst at between 140° C. to 170° C. and pressures ranging from 200 to 5000 psig of hydrogen. The highest weight ratio of diethylenetriamine to piperazine disclosed by U.S. Pat. No. 3,714,259 is 4.5:1 with an average ratio of 3.16:1. British Patent No. 1,508,460 discloses that ethylenediamine will react with itself at a temperature between 100° C. and 150° C. in the presence of iron, nickel, cobalt, palladium, rhodium, ruthenium or platinum. British Patent No. 1,508,460 also discloses that the narrow temperature range of 100° C. to 150° C. is critical because the main product above 150° C. is the cyclized polyalkylene polyamine, piperazine, rather than the linear polyalkylene polyamine, diethylenetriamine.

U.S. Pat. No. 2,861,995 describes a continuous process for the conversion of ethanolamine into multiple nitrogen-containing products, e.g., ethylenediamine, polyethylene polyamines and piperazine, by continuously passing a stream of ethanolamine and ammonia under a pressure of between 1000 and 2500 pounds per square inch over a fixed bed containing a metal hydrogenation catalyst, e.g., nickel, cobalt, copper chromite, platinum and palladium, while the stream is being maintained at a temperature of between about 150° C. and 225° C.

U.S. Pat. No. 4,568,746 discloses a process for the production of an amine composition having a high ratio of diethylenetriamine to piperazine which comprises maintaining ethylenediamine in the presence of a catalyst selected from nickel, cobalt or rhodium, wherein the metal is present on the surface of the catalyst in a polyatomic form, and at a temperature between about 170° C. to about 210° C. sufficient to convert less than about 35% of the amine reactants to polyamine.

U.S. Pat. No. 4,568,746 also discloses a process for the production of an amine composition having a high ratio of diethylenetriamine to piperazine which comprises maintaining a mixture of ethylenediamine and monoethanolamine in the presence of a catalyst selected from nickel, cobalt or rhodium, wherein the metal is present on the surface of the catalyst in a polyatomic form, and at a temperature between about 170° C. and about 210° C. sufficient to convert less than about 35% of the amine reactants to polyamine.

U.S. Pat. No. 4,234,730 discloses a process for preparing a mixture of piperazine and ethylenediamine by the hydrogenation reaction of monoethanolamine and ammonia utilizing a nickel-copper-chromium catalyst. The ratio of ethylenediamine to piperazine in the product mix is predetermined by varying the hydrogen feed rate. It is stated that increasing the hydrogen feed rate causes the ratio of ethylenediamine to piperazine to decrease.

SUMMARY OF THE INVENTION

This invention relates to a method for controlling the weight ratio of diethylenetriamine to piperazine in a process in which ethylenediamine and hydrogen are maintained in the presence of a hydrogenation catalyst, which method comprises adjusting the hydrogen concentration in the liquid phase in an amount sufficient to effectuate control of the weight ratio of diethylenetriamine to piperazine in said process.

This invention also relates to a method for controlling the weight ratio of diethylenetriamine to piperazine in a process in which ethylenediamine, monoethanolamine and hydrogen are maintained in the presence of a hydrogenation catalyst, which method comprises adjusting the hydrogen concentration in the liquid phase in an amount sufficient to effectuate control of the weight ratio of diethylenetriamine to piperazine in said process.

This invention further relates to a process for the production of an amine composition containing a high yield weight ratio of diethylenetriamine to piperazine which comprises (i) maintaining ethylenediamine and hydrogen in the presence of a hydrogenation catalyst, and (ii) adjusting the hydrogen concentration in the liquid phase in an amount sufficient to effectuate a high yield weight ratio of diethylenetriamine to piperazine in said process.

This invention yet further relates to a process for the production of an amine composition containing a high yield weight ratio of diethylenetriamine to piperazine which comprises (i) maintaining ethylenediamine, monoethanolamine and hydrogen in the presence of a hydrogenation catalyst, and (ii) adjusting the hydrogen concentration in the liquid phase in an amount sufficient to effectuate a high yield weight ratio of diethylenetriamine to piperazine in said process.

DETAILED DESCRIPTION

Figure 1:
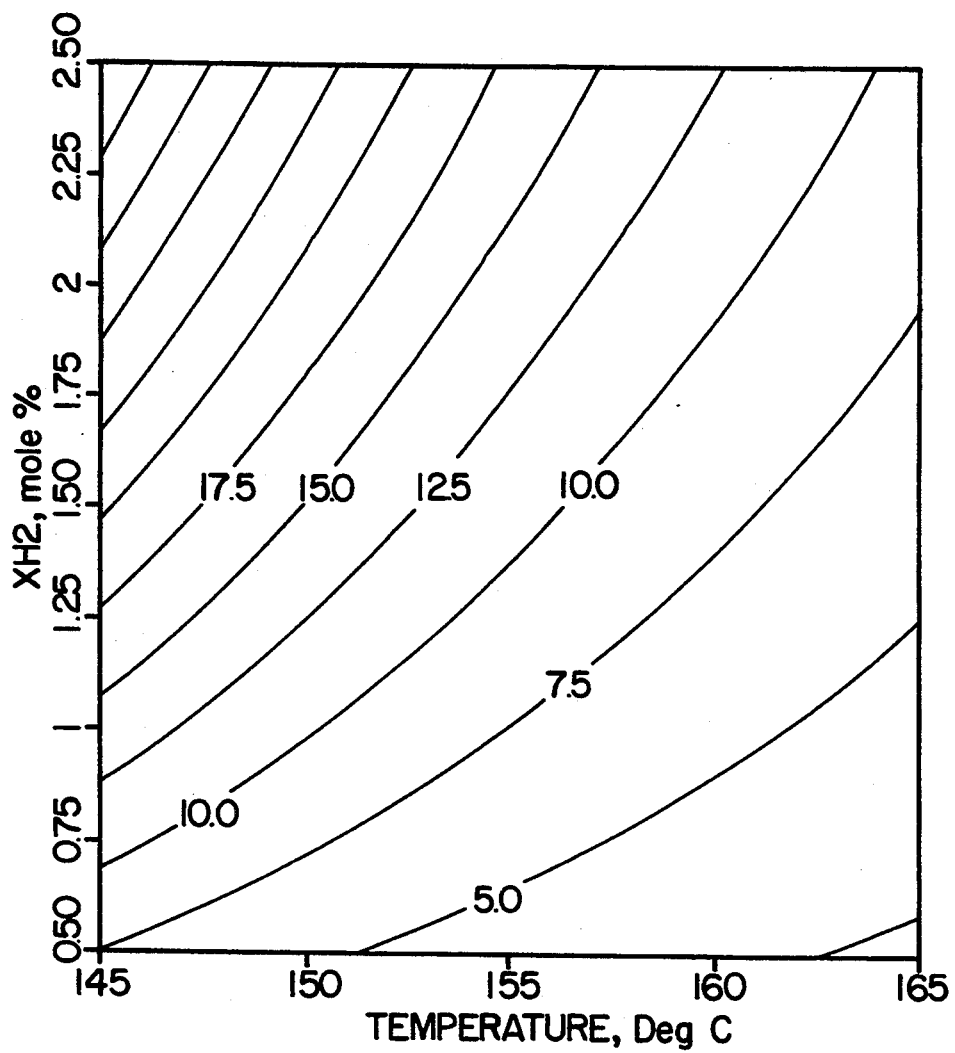
FIG. 1 is a graphical representation of the effect that hydrogen concentration in the liquid phase and temperature have on the weight ratio of diethylenetriamine to piperazine (D/P weight ratio). Contours of constant D/P weight ratio are plotted as a function of hydrogen concentration in the liquid phase and temperature.

As indicated above, this invention relates to a method for controlling the weight ratio of diethylenetriamine to piperazine in a process in which ethylenediamine and hydrogen are maintained in the presence of a hydrogenation catalyst, which method comprises adjusting the hydrogen concentration in the liquid phase in an amount sufficient to effectuate control of the weight ratio of diethylenetriamine to piperazine in said process.

As also indicated above, this invention relates to a method for controlling the weight ratio of diethylenetriamine to piperazine in a process in which ethylenediamine, monoethanolamine and hydrogen are maintained in the presence of a hydrogenation catalyst, which method comprises adjusting the hydrogen concentration in the liquid phase in an amount sufficient to effectuate control of the weight ratio of diethylenetriamine to piperazine in said process.

As further indicated above, this invention relates to a process for the production of an amine composition containing a high yield weight ratio of diethylenetriamine to piperazine which comprises (i) maintaining ethylenediamine and hydrogen in the presence of a hydrogenation catalyst, and (ii) adjusting the hydrogen concentration in the liquid phase in an amount sufficient to effectuate a high yield weight ratio of diethylenetriamine to piperazine in said process.

As yet further indicated above, this invention relates to a process for the production of an amine composition containing a high yield weight ratio of diethylenetriamine to piperazine which comprises (i) maintaining ethylenediamine, monoethanolamine and hydrogen in the presence of a hydrogenation catalyst, and (ii) adjusting the hydrogen concentration in the liquid phase in an amount sufficient to effectuate a high yield weight ratio of diethylenetriamine to piperazine in said process.

It has been found in accordance with this invention that the reaction of ethylenediamine with itself or monoethanolamine in the presence of a hydrogenation catalyst and in the presence of hydrogen in the liquid phase to form ammonia and a polyalkylene polyamine can be controlled so as to adjust the amount of the linear polyalkylene polyamine, diethylenetriamine, that is formed with respect to the amount of the cyclized polyalkylene polyamine, piperazine, that is formed, by varying the hydrogen concentration in the liquid phase.

The reaction is thought to proceed by the condensation of ethylenediamine with itself or monoethanolamine to form diethylenetriamine and a molar equivalent of ammonia or water. The hydrogenation catalyst used to facilitate such a reaction will also catalyze the cyclization of diethylenetriamine to form piperazine and another equivalent of ammonia. Whether the reaction mixture will contain a high ratio of linear to cyclized polyalkylene polyamine is a function of the reaction rates of forming a linear polyalkylene polyamine and the reaction rates of forming a cyclized polyalkylene polyamine from the linear polyalkylene polyamine. The reaction rate of these reactions are dependent upon the catalyst chosen, the concentration of reactants and products, the temperature at which the reaction mixture is maintained, and the hydrogen concentration in the liquid phase. It has been found that when a hydrogenation catalyst is contacted with ethylenediamine or a mixture of ethylenediamine and monoethanolamine in the presence of hydrogen in the liquid phase, the resulting weight ratio of diethylenetriamine to piperazine can be adjusted or controlled by varying the hydrogen concentration in the liquid phase.

FIG. 1 is a graphical representation of the effect that hydrogen concentration in the liquid phase and reaction temperature have on the weight ratio of diethylenetriamine to piperizine (D/P weight ratio). The figure shows that the weight ratio of diethylenetriamine to piperazine decreases with increasing temperature and increases with increasing hydrogen concentration. It is therefore possible to adjust the weight ratio of diethylenetriamine to piperazine by controlling the hydrogen concentration in the liquid phase at the appropriate level. The figure also shows that the magnitude of the effect the hydrogen concentration in the liquid phase has on the weight ratio of diethylenetriamine to piperazine decreases with increasing reaction temperature.

Figure 2:
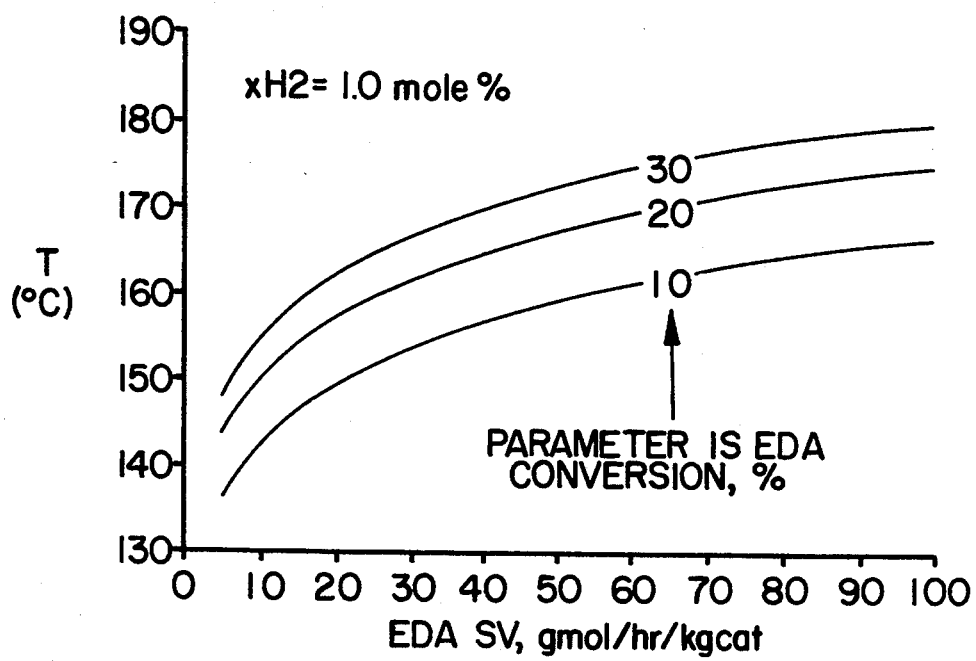
FIG. 2 is a graphical representation of the effect that ethylenediamine space velocity and conversion have on the reaction temperature. The reaction temperature is plotted as a function of ethylenediamine space velocity with ethylenediamine conversion as a parameter and hydrogen concentration in the liquid phase being held constant at 1.0 mole percent.

FIG. 2 is a graphical representation of the effect that ethylenediamine space velocity and conversion have on reaction temperature. The figure shows that the reaction temperature must be increased as the ethylenediamine space velocity increases to maintain a constant conversion of ethylenediamine. The figure also shows that at a constant ethylenediamine space velocity, the reaction temperature must be increased to increase ethylenediamine conversion.

Figure 3:
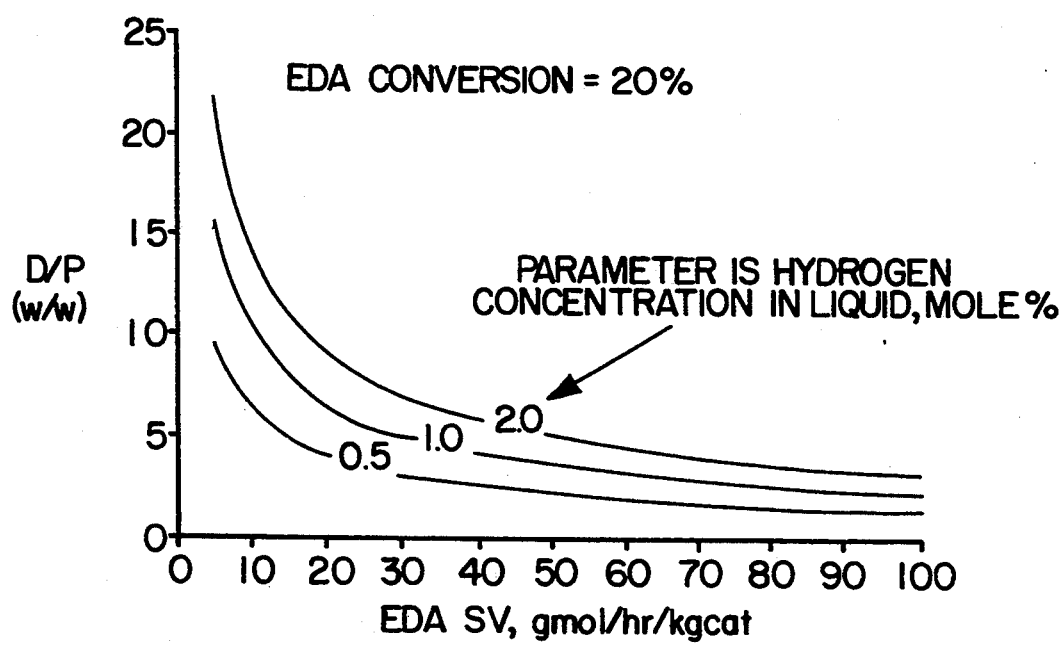
FIG. 3 is a graphical representation of the effect that ethylenediamine space velocity and hydrogen concentration in the liquid phase have on the diethylenetriamine to piperizine weight ratio (D/P weight ratio). The D/P weight ratio is plotted as a function of ethylenediamine space velocity with hydrogen concentration in the liquid phase as a parameter and ethylenediamine conversion being held constant at 20 percent.

FIG. 3 is a graphical representation of the effect that ethylenediamine space velocity and hydrogen concentration in the liquid phase have on the diethylenetriamine to piperazine weight ratio (D/P weight ratio). Like FIG. 1, this figure shows that the weight ratio of diethylenetriamine to piperazine increases as the hydrogen concentration in the liquid phase increases. This figure also shows at constant ethylenediamine conversion, that the weight ratio of diethylenetriamine to piperazine decreases as the ethylenediamine velocity increases.

The reaction temperature and ethylenediamine space velocity are not narrowly critical and can vary over a wide range as illustrated by the figures described above. The monoethanolamine space velocity, when used, is also not narrowly critical and can vary over a wide range. The selection of operating conditions including reaction temperature, ethylenediamine space velocity, monoethanolamine space velocity when used, and hydrogen concentration in the liquid phase is dependent on the desired productivity and selectivity.

The hydrogen concentration in the liquid phase is not narrowly critical and can vary over a wide range as illustrated by the figures described above. It has been found in accordance with this invention that the weight ratio of diethylenetriamine to piperazine can be controlled at a desired value by adjusting the hydrogen concentration in the liquid phase. As illustrated by FIG. 3, the weight ratio of diethylenetriamine to piperazine increases from 4.8 at 0.5 mole percent hydrogen in the liquid phase to 10.8 at 2.0 mole percent hydrogen in the liquid phase at an ethylenediamine space velocity of 15 gram-moles per kilogram of catalyst per hour. In general, a higher concentration of hydrogen in the liquid phase provides for a higher weight ratio of diethylenetriamine to piperazine. The minimum hydrogen concentration in the liquid phase is that concentration necessary to keep the catalyst in an active state.

The method and process described herein are operated at a pressure high enough to insure the presence of a liquid phase. Also, pressure may be used as a manipulated variable to adjust the hydrogen concentration in the liquid phase. To understand how pressure and inerts affect the hydrogen concentration in the liquid phase, consider Henry's law which may be written as:

$$x_i H_i = y_i P$$

where $x_i$ is the mole fraction in the liquid phase, $y_i$ is the mole fraction in the vapor phase, $H_i$ is the Henry's law constant and P is the system pressure. The Henry's law constant is simply a function of temperature. From this expression, it is seen that at a constant temperature, the mole fraction of a component in the liquid phase will increase with increasing system pressure. The addition of an inert, such as nitrogen, will decrease the mole fraction of all other components in the vapor phase. A decrease in the vapor phase mole fraction of a component results in a corresponding decrease of the liquid phase mole fraction. Thus, the weight ratio of diethylenetriamine to piperazine typically increases with system pressure and decreases with inert space velocity. Suitable inerts which can be used in this invention include, for example, nitrogen, methane or any material predominant in the vapor phase.

It should be noted that the mole fraction of hydrogen in the liquid phase will decrease through a tubular reactor because of the generation of ammonia as the reaction proceeds. At the very least, ammonia will behave like an inert in lowering the concentration of hydrogen in the liquid phase. This decrease in liquid phase hydrogen mole fraction throughout the reactor will be more significant as conversion increases and/or hydrogen space velocity decreases.

The catalysts suitable for use in the practice of this invention are hydrogenation catalysts. Hydrogenation catalysts promote the addition of hydrogen to unsaturated carbon-to-carbon linkages. Illustrative of suitable hydrogenation catalysts include, for example, nickel, cobalt, rhodium, copper, iron, palladium, platinum, chromium, molybdenum, titanium and the like which may be relatively pure metal catalysts or catalysts that have been modified by the addition of other transition metals in varying amounts. The catalysts may be in a massive form or they may be supported on a carrier such as the preferred silica or alumina carriers wherein the metal is present on the surface of the catalyst in a polyatomic form. Preferred catalysts are Raney nickel and Raney cobalt (available from Davison Chemical) or a nickel/rhenium/boron on silica catalyst prepared as described in U.S. Pat. No. 4,123,462.

The amount of catalyst employed is not narrowly critical as illustrated by FIG. 2 and FIG. 3 described above. In these figures, the ethylenediamine space velocity is defined as the molar flow rate of ethylenediamine per unit weight of catalyst charge. Once the catalyst charge has been established, the molar flow rate of ethylenediamine, monoethanolamine when used, reaction temperature and hydrogen concentration in the liquid phase are set to give the desired results. If the method or process is conducted in a batchwise fashion, the ethylenediamine charge, monoethanolamine charge when used, and reaction time are set as opposed to the molar flow rates of ethylenediamine and monoethanolamine when used.

When ethylenediamine is the sole organic reactant, the amine composition which is obtained by the practice of the present invention will be a mixture of unreacted ethylenediamine, the desired diethylenetriamine, piperazine, and minor amounts of other reaction products such as aminoethylpiperazine and higher polyethylene polyamines. This amine composition may then be distilled to yield the desired diethylenetriamine in a more purified form.

When a mixture of ethylenediamine and monoethanolamine is employed, the amine composition which is obtained by the practice of the present invention will be a mixture of unreacted ethylenediamine and monoethanolamine, the desired diethylenetriamine, piperazine, and minor amounts of other reaction products such as aminoethylethanolamine, aminoethylpiperazine and higher polyethylene polyamines. This amine composition may then be distilled to yield the desired diethylenetriamine in a more purified form.

The practice of this invention provides the ability to selectively generate the manufacture of diethylenetriamine without generating large amounts of cyclic polyalkylene polyamine products such as piperazine, aminoethylpiperazine and hydroxyethylpiperazine. A significant advantage afforded by this invention is the flexibility to attain desired weight ratios of diethylenetriamine to piperazine by adjusting the hydrogen concentration in the liquid phase.

The reaction described herein may be effected by the incremental addition of any of the starting materials or by the joint addition of any of the starting materials to the catalyst. The preferred process effects the reaction in a continuous manner over a fixed bed of the catalyst in a tubular reactor. However, the reaction may be carried out by slurrying the catalyst in the reactant(s) or in a batch mode in an autoclave.

The method of this invention is preferably carried out at a temperature of from about 50° C. to about 300° C., at a pressure of from about atmospheric to about 5000 psig, and maintaining ethylenediamine at a space velocity of from about 1 to about 500 gram-moles per kilogram of catalyst per hour.

The following abbreviations have the indicated meanings herein:
EDA Ethylenediamine
EtEDA Ethylethylenediamine
PIP Piperazine
DETA Diethylenetriamine
AEP Aminoethylpoperazine
1-TETA Triethylenetetraamine
1-TEPA Tetraethylenepentaamine
D/P Diethylenetriamine/Piperazine
SV Space Velocity This invention is further illustrated by the following examples.

EXAMPLES

The reactor used in the experimental runs set forth in Tables I and II below consisted of a 74.75 inch-long Type 316 stainless steel medium pressure tube of 0.688 inch i.d. and 1.0 inch o.d. The temperature in the reaction zone was measured by three thermocouples evenly distributed in the reaction zone and placed in a ⅛ inch o.d. thermowell located in the center of the tube. 200 grams of catalyst containing 6.2 weight percent nickel, 4.4 weight percent rhenium and 1.8 weight percent boron were charged to the reactor. The free volume remaining in the tube was filled with an inert material of similar size to the catalyst. Heating was supplied through the wall of the tube (when necessary) by three individually controlled heat tapes. EDA was pumped to the system and passed through a preheater. Hydrogen (and nitrogen when used) was fed to the system and passed through a second preheater. The hydrogen (and nitrogen) was then mixed with the EDA, and this mixture was passed through a third preheater prior to entering the reaction zone.

The reaction mixture was passed through the reaction zone in a downflow fashion. The pressure in the reaction zone was controlled by a motor valve at the outlet of the reactor. After leaving the reaction zone the pressure of the stream was reduced from that of the reaction zone to slightly above atmospheric. This stream was then passed through a wet ice trap where the hydrogen was separated from the condensables which were collected in a semi-batch fashion. Ammonia was stripped from this mixture by semi-batch distillation leaving a mixture containing unreacted EDA and the products of the reaction. The mixture of unreacted EDA and products of the reaction was then analyzed for water by a Karl-Fisher procedure and for organics (amines) by capillary gas chromatography.

The examples set forth in Tables I and II demonstrate this invention. Expressions derived from these examples were used to generate FIGS. 1, 2 and 3 herein.

TABLE I

| Example No. | | 1 | 2 | 3 | 4 | 5 | 6 | 7 | 8 | 9 |
|---|---|---|---|---|---|---|---|---|---|---|
| EDA SV, gmol/hr/kgcat | | 15.54 | 15.89 | 15.30 | 10.53 | 10.74 | 10.64 | 21.03 | 19.84 | 21.93 |
| H2 SV, gmol/hr/kgcat | | 6.25 | 6.25 | 5.73 | 8.92 | 9.82 | 8.81 | 5.38 | 8.57 | 9.82 |
| Pressure, psia | | 314.7 | 314.7 | 314.7 | 514.7 | 514.7 | 514.7 | 119.7 | 119.7 | 114.7 |
| EDA Conversion, % | | 14.44 | 19.75 | 8.62 | 9.50 | 13.75 | 6.60 | 13.10 | 16.80 | 13.62 |
| Time on Organics, hrs | | 632 | 637 | 656 | 680 | 685 | 705 | 725 | 750 | 776 |
| Temperature, °C. | | 146.8 | 150.6 | 141.8 | 142.4 | 146.8 | 138.2 | 151.4 | 156.4 | 147.2 |
| D/P Weight Ratio | | 7.79 | 5.88 | 10.63 | 12.27 | 9.33 | 15.62 | 1.23 | 0.97 | 1.94 |
| Carbon Balance, % | | 97.4 | 95.3 | 100.1 | 98.0 | 99.1 | 101.6 | 94.9 | 97.3 | 94.1 |
| Condensed | EDA | 87.628 | 83.018 | 92.634 | 91.859 | 88.191 | 94.347 | 89.400 | 86.424 | 88.782 |
| Product | EtEDA | 0.006 | 0.007 | 0.004 | 0.003 | 0.005 | 0.004 | 0.006 | 0.009 | 0.007 |
| Composition | PIP | 1.304 | 2.247 | 0.613 | 0.593 | 1.081 | 0.332 | 4.447 | 6.324 | 3.524 |
| (wt %) | DETA | 10.153 | 13.221 | 6.511 | 7.271 | 10.088 | 5.186 | 5.457 | 6.106 | 6.850 |
| | AEP | 0.085 | 0.180 | 0.021 | 0.025 | 0.050 | 0.009 | 0.354 | 0.609 | 0.406 |
| | 1-TETA | 0.796 | 1.238 | 0.217 | 0.249 | 0.585 | 0.121 | 0.335 | 0.528 | 0.431 |
| | 1-TEPA | 0.029 | 0.088 | 0.000 | 0.000 | 0.000 | 0.000 | 0.000 | 0.000 | 0.000 |
| Component | EtEDA | 0.0006 | 0.0008 | 0.0004 | 0.0002 | 0.0003 | 0.0003 | 0.0009 | 0.0011 | 0.0009 |
| Productivities | PIP | 0.1380 | 0.2409 | 0.0645 | 0.0429 | 0.0792 | 0.0244 | 0.6344 | 0.8430 | 0.5246 |
| (gmol/hr/kgcat) | DETA | 0.8974 | 1.1828 | 0.5721 | 0.4393 | 0.6172 | 0.3182 | 0.6498 | 0.6793 | 0.8512 |
| | AEP | 0.0060 | 0.0129 | 0.0015 | 0.0012 | 0.0025 | 0.0004 | 0.0337 | 0.0541 | 0.0403 |
| | 1-TETA | 0.0496 | 0.0782 | 0.0135 | 0.0106 | 0.0252 | 0.0053 | 0.0281 | 0.0415 | 0.0378 |
| | 1-TEPA | 0.0014 | 0.0043 | 0.0000 | 0.0000 | 0.0000 | 0.0000 | 0.0000 | 0.0000 | 0.0000 |
| H2 Concentration in Liquid, mole % | | 0.446 | 0.452 | 0.437 | 0.747 | 0.765 | 0.730 | 0.132 | 0.127 | 0.127 |

| Example No. | | 10 | 11 | 12 | 13 | 14 | 15 | 16 | 17 | 18 |
|---|---|---|---|---|---|---|---|---|---|---|
| EDA SV, gmol/hr/kgcat | | 19.79 | 20.42 | 20.05 | 12.50 | 11.76 | 12.51 | 15.11 | 15.37 | 14.78 |
| H2 SV, gmol/hr/kgcat | | 2.21 | 2.14 | 2.10 | 1.63 | 1.83 | 1.78 | 6.13 | 5.73 | 5.98 |
| Pressure, psia | | 514.7 | 514.7 | 514.7 | 114.7 | 114.7 | 114.7 | 314.7 | 314.7 | 314.7 |
| EDA Conversion, % | | 14.25 | 21.35 | 9.89 | 10.67 | 13.50 | 6.94 | 14.00 | 18.59 | 8.55 |
| Time on Organics, hrs | | 800 | 806 | 824 | 848 | 854 | 872.1 | 896 | 901 | 920 |
| Temperature, °C. | | 152.4 | 157.1 | 148 | 141.2 | 145.7 | 136.4 | 147 | 151.5 | 142.7 |
| D/P Weight Ratio | | 7.85 | 5.23 | 10.61 | 2.87 | 1.60 | 3.28 | 7.24 | 5.28 | 8.34 |
| Carbon Balance, % | | 100.9 | 97.8 | 99.6 | 99.8 | 99.0 | 94.4 | 96.9 | 95.3 | 99.6 |
| Condensed | EDA | 87.790 | 81.639 | 91.542 | 91.129 | 88.950 | 94.242 | 88.023 | 84.079 | 92.728 |
| Product | EtEDA | 0.004 | 0.007 | 0.001 | 0.006 | 0.006 | 0.004 | 0.004 | 0.007 | 0.004 |
| Composition | PIP | 1.290 | 2.671 | 0.697 | 2.201 | 4.009 | 1.315 | 1.378 | 2.347 | 0.753 |
| (wt %) | DETA | 10.123 | 13.977 | 7.390 | 6.315 | 6.429 | 4.315 | 9.974 | 12.380 | 6.287 |
| | AEP | 0.075 | 0.228 | 0.031 | 0.098 | 0.241 | 0.036 | 0.076 | 0.182 | 0.028 |
| | 1-TETA | 0.718 | 1.356 | 0.338 | 0.251 | 0.365 | 0.087 | 0.546 | 1.006 | 0.200 |
| | 1-TEPA | 0.000 | 0.123 | 0.000 | 0.000 | 0.000 | 0.000 | 0.000 | 0.000 | 0.000 |
| Component | EtEDA | 0.0005 | 0.0009 | 0.0002 | 0.0005 | 0.0005 | 0.0003 | 0.0005 | 0.0007 | 0.0004 |
| Productivities | PIP | 0.1740 | 0.3665 | 0.0959 | 0.1883 | 0.3199 | 0.1134 | 0.1419 | 0.2437 | 0.0766 |
| (gmol/hr/kgcat) | DETA | 1.1397 | 1.6012 | 0.8493 | 0.4508 | 0.4283 | 0.3106 | 0.8576 | 1.0730 | 0.5338 |
| | AEP | 0.0068 | 0.0208 | 0.0028 | 0.0056 | 0.0128 | 0.0021 | 0.0052 | 0.0126 | 0.0019 |
| | 1-TETA | 0.0571 | 0.1096 | 0.0275 | 0.0126 | 0.0171 | 0.0044 | 0.0331 | 0.0615 | 0.0120 |
| | 1-TEPA | 0.0000 | 0.0077 | 0.0000 | 0.0000 | 0.0000 | 0.0000 | 0.0000 | 0.0000 | 0.0000 |

TABLE I-continued

| | | | | | | | | | |
|---|---|---|---|---|---|---|---|---|---|
| H2 Concentration in Liquid, mole % | | 0.786 | 0.803 | 0.770 | 0.130 | 0.128 | 0.131 | 0.446 | 0.453 | 0.439 |

TABLE II

| Example No. | | 19 | 20 | 21 | 22 | 23 | 24 | 25 | 26 | 27 |
|---|---|---|---|---|---|---|---|---|---|---|
| EDA SV, gmol/hr/kgcat | | 15.09 | 15.43 | 15.19 | 10.57 | 10.49 | 10.56 | 10.27 | 10.75 | 10.15 |
| H2 SV, gmol/hr/kgcat | | 6.07 | 6.22 | 5.24 | 9.53 | 9.53 | 9.06 | 2.14 | 2.39 | 2.10 |
| N2 SV, gmol/hr/kgcat | | 0.00 | 0.00 | 0.00 | 0.00 | 0.00 | 0.00 | 0.00 | 0.00 | 0.00 |
| Pressure, psia | | 614.7 | 614.7 | 614.7 | 914.7 | 914.7 | 914.7 | 314.7 | 314.7 | 314.7 |
| EDA Conversion, % | | 17.69 | 25.61 | 11.27 | 12.94 | 27.59 | 5.25 | 14.46 | 29.86 | 5.02 |
| Time on Organics, hrs | | 943.8 | 950 | 968 | 992 | 1014.9 | 1041 | 1067 | 1071 | 1089 |
| Temperature, °C. | | 153.2 | 157.2 | 147.2 | 148.2 | 157.2 | 139 | 143.4 | 153.1 | 135.1 |
| D/P Weight Ratio | | 7.90 | 5.57 | 12.32 | 13.83 | 6.14 | 22.31 | 8.00 | 3.89 | 9.76 |
| Carbon Balance, % | | 97.0 | 96.0 | 99.7 | 99.2 | 98.3 | 94.5 | 89.9 | 94.4 | 95.1 |
| Condensed Product Composition (wt %) | EDA | 84.754 | 77.794 | 90.319 | 88.843 | 75.955 | 95.498 | 87.595 | 74.099 | 95.741 |
| | EtEDA | 0.005 | 0.008 | 0.004 | 0.003 | 0.007 | 0.003 | 0.004 | 0.009 | 0.002 |
| | PIP | 1.586 | 2.996 | 0.692 | 0.717 | 2.971 | 0.190 | 1.305 | 4.563 | 0.392 |
| | DETA | 12.535 | 16.676 | 8.532 | 9.914 | 18.249 | 4.230 | 10.442 | 18.097 | 3.828 |
| | AEP | 0.107 | 0.299 | 0.031 | 0.030 | 0.266 | 0.000 | 0.063 | 0.497 | 0.010 |
| | 1-TETA | 0.963 | 2.010 | 0.421 | 0.493 | 2.249 | 0.080 | 0.591 | 2.378 | 0.026 |
| | 1-TEPA | 0.050 | 0.218 | 0.000 | 0.000 | 0.304 | 0.000 | 0.000 | 0.267 | 0.000 |
| Component Productivities (gmol/hr/kgcat) | EtEDA | 0.0005 | 0.0008 | 0.0004 | 0.0002 | 0.0005 | 0.0002 | 0.0003 | 0.0006 | 0.0002 |
| | PIP | 0.1622 | 0.3083 | 0.0721 | 0.0518 | 0.2073 | 0.0139 | 0.0913 | 0.3303 | 0.0276 |
| | DETA | 1.0697 | 1.4325 | 0.7415 | 0.5979 | 1.0629 | 0.2581 | 0.6100 | 1.0721 | 0.2245 |
| | AEP | 0.0073 | 0.0205 | 0.0022 | 0.0014 | 0.0124 | 0.0000 | 0.0030 | 0.0235 | 0.0005 |
| | 1-TETA | 0.0580 | 0.1219 | 0.0258 | 0.0210 | 0.0925 | 0.0034 | 0.0244 | 0.0994 | 0.0011 |
| | 1-TEPA | 0.0023 | 0.0102 | 0.0000 | 0.0000 | 0.0096 | 0.0000 | 0.0000 | 0.0086 | 0.0000 |
| H2 Concentration in Liquid, mole % | | 0.956 | 0.975 | 0.927 | 1.415 | 1.489 | 1.336 | 0.440 | 0.456 | 0.424 |

| Example No. | | 28 | 29 | 30 | 31 | 32 | 33 | 34 | 35 | 36 |
|---|---|---|---|---|---|---|---|---|---|---|
| EDA SV, gmol/hr/kgcat | | 20.34 | 21.26 | 20.45 | 18.89 | 19.06 | 18.35 | 17.72 | 16.93 | 18.49 |
| H2 SV, gmol/hr/kgcat | | 2.07 | 2.07 | 1.90 | 9.95 | 10.13 | 9.46 | 2.01 | 2.43 | 2.68 |
| N2 SV, gmol/hr/kgcat | | 0.00 | 0.00 | 0.00 | 0.00 | 0.00 | 0.00 | 9.82 | 10.35 | 10.33 |
| Pressure, psia | | 914.7 | 914.7 | 914.7 | 314.7 | 314.7 | 314.7 | 314.7 | 314.7 | 314.7 |
| EDA Conversion, % | | 13.81 | 27.61 | 5.55 | 16.74 | 28.61 | 7.21 | 10.76 | 15.30 | 5.88 |
| Time on Organics, hrs | | 1113 | 1118.5 | 1137 | 1233 | 1238.4 | 1257 | 1305.5 | 1329 | 1352 |
| Temperature, °C. | | 155.2 | 164.5 | 145.7 | 150.7 | 159.5 | 141.3 | 150.9 | 160.2 | 142.1 |
| D/P Weight Ratio | | 10.67 | 4.96 | 19.44 | 6.13 | 3.30 | 10.62 | 0.97 | 0.54 | 1.33 |
| Carbon Balance, % | | 95.7 | 94.7 | 97.6 | 98.6 | 95.2 | 101.1 | 101.4 | 97.3 | 99.9 |
| Condensed Product Composition (wt %) | EDA | 88.125 | 76.050 | 95.246 | 85.666 | 75.357 | 93.851 | 91.409 | 87.916 | 95.295 |
| | EtEDA | 0.004 | 0.008 | 0.002 | 0.004 | 0.008 | 0.002 | 0.004 | 0.007 | 0.000 |
| | PIP | 0.945 | 3.444 | 0.228 | 1.850 | 4.938 | 0.513 | 4.118 | 7.195 | 1.959 |
| | DETA | 10.082 | 17.086 | 4.434 | 11.347 | 16.280 | 5.447 | 3.975 | 3.907 | 2.596 |
| | AEP | 0.059 | 0.424 | 0.006 | 0.139 | 0.668 | 0.019 | 0.199 | 0.452 | 0.053 |
| | 1-TETA | 0.745 | 2.559 | 0.084 | 0.949 | 2.399 | 0.168 | 0.294 | 0.523 | 0.097 |
| | 1-TEPA | 0.040 | 0.428 | 0.000 | 0.045 | 0.349 | 0.000 | 0.000 | 0.000 | 0.000 |
| Component Productivities (gmol/hr/kgcat) | EtEDA | 0.0005 | 0.0011 | 0.0003 | 0.0005 | 0.0010 | 0.0003 | 0.0005 | 0.0008 | 0.0000 |
| | PIP | 0.1312 | 0.4862 | 0.0323 | 0.2371 | 0.6221 | 0.0649 | 0.4970 | 0.8191 | 0.2496 |
| | DETA | 1.1679 | 2.0132 | 0.5236 | 1.2135 | 1.7117 | 0.5754 | 0.4005 | 0.3712 | 0.2762 |
| | AEP | 0.0054 | 0.0399 | 0.0006 | 0.0119 | 0.0561 | 0.0016 | 0.0160 | 0.0343 | 0.0045 |
| | 1-TETA | 0.0609 | 0.2128 | 0.0070 | 0.0716 | 0.1780 | 0.0125 | 0.0209 | 0.0351 | 0.0072 |
| | 1-TEPA | 0.0025 | 0.0275 | 0.0000 | 0.0026 | 0.0200 | 0.0000 | 0.0000 | 0.0000 | 0.0000 |
| H2 Concentration in Liquid, mole % | | 1.473 | 1.547 | 1.394 | 0.452 | 0.463 | 0.436 | 0.077 | 0.088 | 0.090 |

| Example No. | | 37 | 38 | 39 | 40 | 41 | 42 |
|---|---|---|---|---|---|---|---|
| EDA SV, gmol/hr/kgcat | | 9.93 | 10.65 | 10.51 | 14.76 | 15.34 | 14.78 |
| H2 SV, gmol/hr/kgcat | | 2.23 | 2.23 | 2.03 | 6.38 | 6.18 | 6.13 |
| N2 SV, gmol/hr/kgcat | | 8.39 | 5.84 | 8.70 | 0.00 | 0.00 | 0.00 |
| Pressure, psia | | 914.7 | 914.7 | 914.7 | 614.7 | 614.7 | 614.7 |
| EDA Conversion, % | | 20.22 | 31.83 | 10.72 | 12.97 | 25.50 | 5.45 |
| Time on Organics, hrs | | 1404 | 1408 | 1425.5 | 1450 | 1456 | 1484.3 |
| Temperature, °C. | | 147.5 | 156.6 | 139.1 | 149.7 | 158.6 | 140 |
| D/P Weight Ratio | | 3.92 | 2.96 | 6.25 | 11.27 | 5.69 | 15.73 |
| Carbon Balance, % | | 102.2 | 95.3 | 96.6 | 100.3 | 97.6 | 99.0 |
| Condensed Product Composition (wt %) | EDA | 82.756 | 72.476 | 90.897 | 88.848 | 77.886 | 95.347 |
| | EtEDA | 0.006 | 0.009 | 0.000 | 0.000 | 0.007 | 0.000 |
| | PIP | 3.219 | 6.062 | 1.203 | 0.860 | 2.931 | 0.271 |
| | DETA | 12.613 | 17.967 | 7.520 | 9.694 | 16.690 | 4.262 |
| | AEP | 0.266 | 0.790 | 0.060 | 0.045 | 0.298 | 0.015 |
| | 1-TETA | 1.087 | 2.432 | 0.320 | 0.553 | 1.961 | 0.105 |
| | 1-TEPA | 0.053 | 0.265 | 0.000 | 0.000 | 0.228 | 0.000 |
| Component Productivities (gmol/hr/kgcat) | EtEDA | 0.0004 | 0.0006 | 0.0000 | 0.0000 | 0.0007 | 0.0000 |
| | PIP | 0.2150 | 0.4239 | 0.0866 | 0.0868 | 0.3001 | 0.0277 |
| | DETA | 0.7033 | 1.0486 | 0.4520 | 0.8164 | 1.4264 | 0.3639 |
| | AEP | 0.0119 | 0.0369 | 0.0029 | 0.0030 | 0.0204 | 0.0010 |
| | 1-TETA | 0.0428 | 0.1002 | 0.0136 | 0.0329 | 0.1183 | 0.0063 |
| | 1-TEPA | 0.0016 | 0.0084 | 0.0000 | 0.0000 | 0.0106 | 0.0000 |
| H2 Concentration | | 0.296 | 0.410 | 0.253 | 0.939 | 0.981 | 0.889 |

Although the invention has been illustrated by the preceding examples, it is not to be construed as being limited thereby, but rather, the invention encompasses the generic area as hereinbefore disclosed. Various modifications and embodiments can be made without departing from the spirit and scope thereof.

It is claimed:

1. A method for controlling the weight ratio of diethylenetriamine to piperazine in a process in which ethylenediamine and hydrogen are maintained in the presence of a hydrogenation catalyst, which method comprises adjusting the hydrogen concentration in the liquid phase in an amount sufficient to effectuate control of the weight ratio of diethylenetriamine to piperazine in said process.

2. The method of claim 1 wherein the catalyst is selected from nickel, cobalt or rhodium.

3. The method of claim 1 wherein the catalyst is Raney nickel.

4. The method of claim 1 wherein the catalyst is Raney cobalt.

5. The method of claim 1 wherein the catalyst is nickel/rhenium/boron.

6. The method of claim 1 wherein pressure is used to adjust the hydrogen concentration in the liquid phase.

7. The method of claim 1 wherein an inert in either the vapor or liquid phase is used to adjust the hydrogen concentration in the liquid phase.

8. The method of claim 1 which is carried out at a temperature of from about 50° C. to about 300° C.

9. The method of claim 1 which is carried out at a pressure of from about atmospheric to about 5000 psig.

10. The method of claim 1 wherein ethylenediamine is maintained at a space velocity of from about 1 to about 500 gram-moles per kilogram of catalyst per hour.

11. A method for controlling the weight ratio of diethylenetriamine to piperazine in a process in which a mixture of ethylenediamine, monoethanolamine and hydrogen are maintained in the presence of a hydrogenation catalyst, which method comprises adjusting the hydrogen concentration in the liquid phase in an amount sufficient to effectuate control of the weight ratio of diethylenetriamine to piperazine in said process.

12. The method of claim 11 wherein the catalyst is selected from nickel, cobalt or rhodium.

13. The method of claim 11 wherein the catalyst is Raney nickel.

14. The method of claim 11 wherein the catalyst is Raney cobalt.

15. The method of claim 11 wherein the catalyst is nickel/rhenium/boron.

16. The method of claim 11 wherein pressure is used to adjust the hydrogen concentration in the liquid phase.

17. The method of claim 11 wherein an inert in either the vapor or liquid phase is used to adjust the hydrogen concentration in the liquid phase.

18. The method of claim 11 which is carried out at a temperature of from about 50° C. to about 300° C.

19. The method of claim 11 which is carried out at a pressure of from about atmospheric to about 5000 psig.

20. The method of claim 11 wherein ethylenediamine is maintained at a space velocity of from about 1 to about 500 gram-moles per kilogram of catalyst per hour.

21. The method of claim 11 wherein monoethanolamine is maintained at a space velocity of from about 1 to about 500 gram-moles per kilogram of catalyst per hour.

22. A method for increasing the weight ratio of diethylenetriamine to piperazine at constant Ethylenediamine conversion and constant space velocity in a process in which ethylenediamine and hydrogen are maintained in the presence of a hydrogenation catalyst, which method comprises increasing the hydrogen concentration in the liquid phase in an amount sufficient to effectuate control of the weight ratio of diethylenetriamine to piperazine in said process.

23. The method of claim 22 wherein the catalyst is selected from nickel, cobalt or rhodium.

24. The method of claim 22 wherein the catalyst is Raney nickel.

25. The method of claim 22 wherein the catalyst is Raney cobalt.

26. The method of claim 22 wherein the catalyst is nickel/rhenium/boron.

27. The method of claim 22 wherein pressure is used to adjust the hydrogen concentration in the liquid phase.

28. The method of claim 22 wherein an inert in either the vapor or liquid phase is used to adjust the hydrogen concentration in the liquid phase.

29. The method of claim 22 which is carried out at a temperature of from about 50° C. to about 300° C.

30. The method of claim 22 which is carried out at a pressure of from about atmospheric to about 5000 psig.

31. The method of claim 22 wherein ethylenediamine is maintained at a space velocity of from about 1 to about 500 gram-moles per kilogram of catalyst per hour.

* * * * *